United States Patent [19]
Yoon

[11] Patent Number: 5,919,202
[45] Date of Patent: Jul. 6, 1999

[54] SURGICAL INSTRUMENT WITH JAWS AND MOVABLE INTERNAL NEEDLE AND METHOD FOR USE THEREOF

[76] Inventor: InBae Yoon, 2101 Highland Ridge Dr., Phoenix, Md. 21131

[*] Notice: This patent is subject to a terminal disclaimer.

[21] Appl. No.: 08/847,190

[22] Filed: May 1, 1997

Related U.S. Application Data

[63] Continuation-in-part of application No. 08/376,186, Jan. 20, 1995, Pat. No. 5,665,100, which is a continuation-in-part of application No. 08/281,814, Jul. 28, 1994, abandoned, which is a continuation of application No. 08/073,193, Jun. 8, 1993, Pat. No. 5,334,209, which is a continuation of application No. 07/720,381, Jun. 25, 1991, Pat. No. 5,217,473, which is a division of application No. 07/446,555, Dec. 5, 1989, Pat. No. 5,026,379.

[51] Int. Cl.$^6$ .................................................... A61B 17/22
[52] U.S. Cl. ........................ 606/170; 606/205; 606/139; 606/144
[58] Field of Search ..................................... 606/205, 207, 606/151, 170, 142, 144, 139, 149, 148, 167

[56] References Cited

U.S. PATENT DOCUMENTS

| | | |
|---|---|---|
| 2,002,594 | 5/1935 | Wappler et al. . |
| 2,004,559 | 6/1935 | Wappler et al. . |
| 2,028,635 | 1/1936 | Wappler . |
| 4,077,412 | 3/1978 | Moossun . |
| 4,103,680 | 8/1978 | Yoon . |
| 4,174,715 | 11/1979 | Hasson . |
| 4,249,533 | 2/1981 | Komiya . |
| 4,257,420 | 3/1981 | Terayama . |
| 4,372,295 | 2/1983 | Heckele . |
| 4,374,523 | 2/1983 | Yoon . |
| 4,393,872 | 7/1983 | Reznik et al. . |
| 4,427,014 | 1/1984 | Bel et al. . |
| 4,471,766 | 9/1984 | Terayama . |
| 4,557,255 | 12/1985 | Goodman . |
| 4,598,699 | 7/1986 | Garren et al. . |
| 4,788,966 | 12/1988 | Yoon . |
| 4,869,268 | 9/1989 | Yoon . |
| 4,966,583 | 10/1990 | Debbas . |
| 5,025,778 | 6/1991 | Silverstein et al. . |
| 5,037,433 | 8/1991 | Wilk et al. . |
| 5,139,487 | 8/1992 | Baber . |
| 5,147,373 | 9/1992 | Ferzli . |
| 5,176,695 | 1/1993 | Dulebohn . |
| 5,190,541 | 3/1993 | Abele et al. . |
| 5,211,650 | 5/1993 | Noda . |
| 5,217,460 | 6/1993 | Knoepfler . |
| 5,226,908 | 7/1993 | Yoon . |
| 5,234,443 | 8/1993 | Phan et al. . |

(List continued on next page.)

*Primary Examiner*—Michael Buiz
*Assistant Examiner*—Daphna Shai
*Attorney, Agent, or Firm*—Blank Rome Comisky & McCauley LLP

[57] ABSTRACT

A surgical instrument includes a forceps unit for being positioned within an anatomical cavity and inner member having a needle on a distal end thereof. The forceps unit includes a housing, an outer tubular member, an intermediate member, and a handle mechanism coupled with at least one of the intermediate and outer tubular members for creating relative movement between the intermediate and outer tubular members. The intermediate member has a tubular body disposed telescopically within the outer tubular member, a proximal end mounted on the housing and an integral one-piece distal end defining a pair of opposed jaws resiliently biased apart such that relative movement of the outer tubular member distally over the jaws causes the jaws to close. The inner member includes a tubular member slidably disposed at least partly within the intermediate member and carrying a needle for performing at least one of the functions of manipulating, dissecting, collecting tissue for biopsy, penetrating tissue, injecting fluids, creating suction, aspirating, irrigating, and cauterizing, or the like.

31 Claims, 11 Drawing Sheets

U.S. PATENT DOCUMENTS

| | | |
|---|---|---|
| 5,261,917 | 11/1993 | Hasson et al. . |
| 5,312,391 | 5/1994 | Wilk . |
| 5,318,589 | 6/1994 | Lichtman . |
| 5,324,254 | 6/1994 | Phillips . |
| 5,336,231 | 8/1994 | Adair . |
| 5,348,555 | 9/1994 | Zinnanti . |
| 5,366,476 | 11/1994 | Noda . |
| 5,398,670 | 3/1995 | Ortiz et al. . |
| 5,403,332 | 4/1995 | Christoudias . |
| 5,462,561 | 10/1995 | Voda . |
| 5,462,562 | 10/1995 | Elkus . |
| 5,476,505 | 12/1995 | Limon . |
| 5,496,310 | 3/1996 | Exconde et al. . |
| 5,538,008 | 7/1996 | Crowe . |
| 5,542,949 | 8/1996 | Yoon . |
| 5,549,623 | 8/1996 | Sharpe et al. . |
| 5,562,102 | 10/1996 | Taylor . |
| 5,569,241 | 10/1996 | Edwards . |
| 5,578,007 | 11/1996 | Imran . |
| 5,607,435 | 3/1997 | Sachdeva et al. . |
| 5,611,813 | 3/1997 | Lichtman . |
| 5,620,459 | 4/1997 | Lichtman . |
| 5,746,770 | 5/1998 | Zeitels et al. . |
| 5,766,169 | 6/1998 | Fritzsch et al. . |

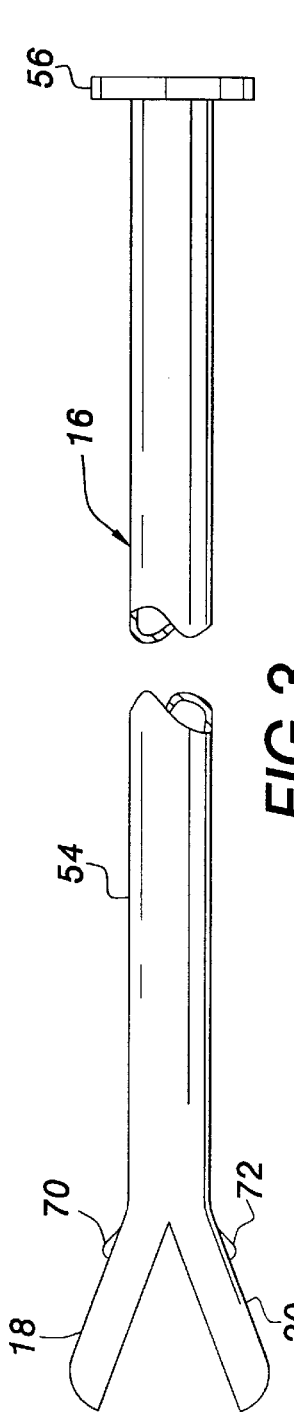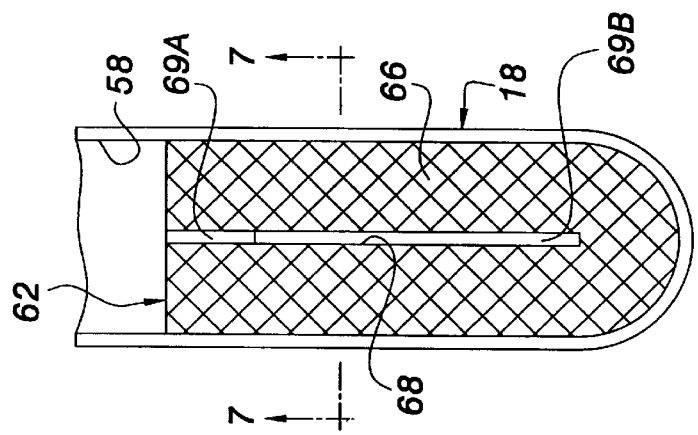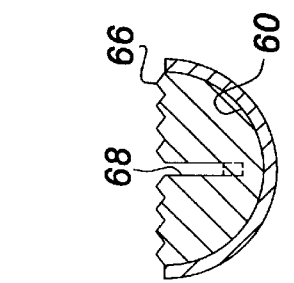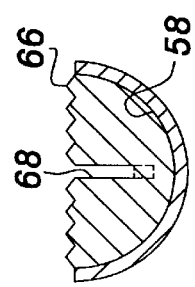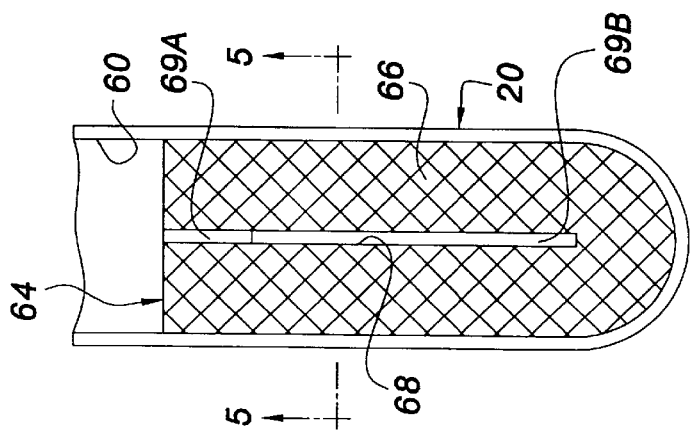

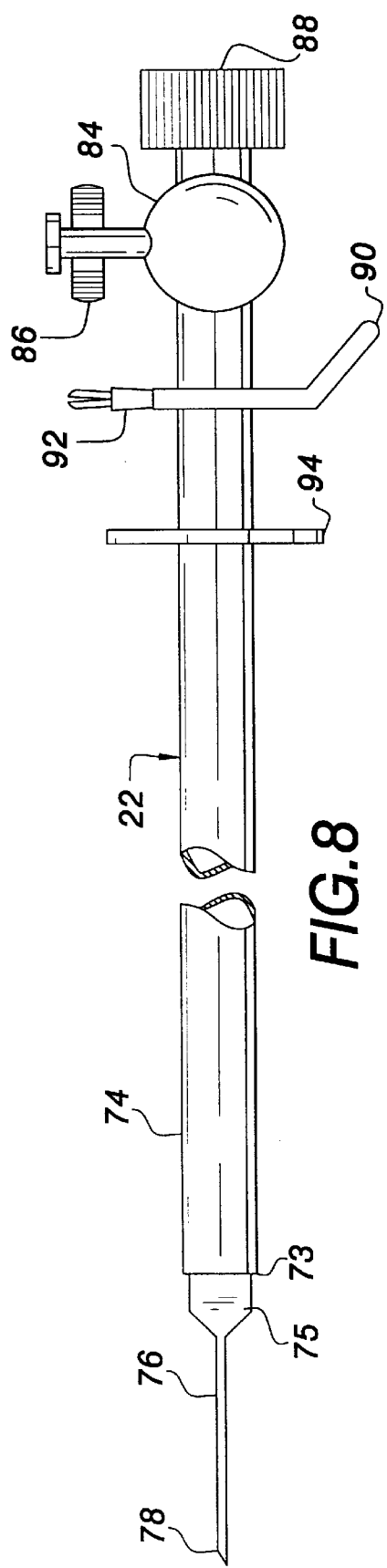
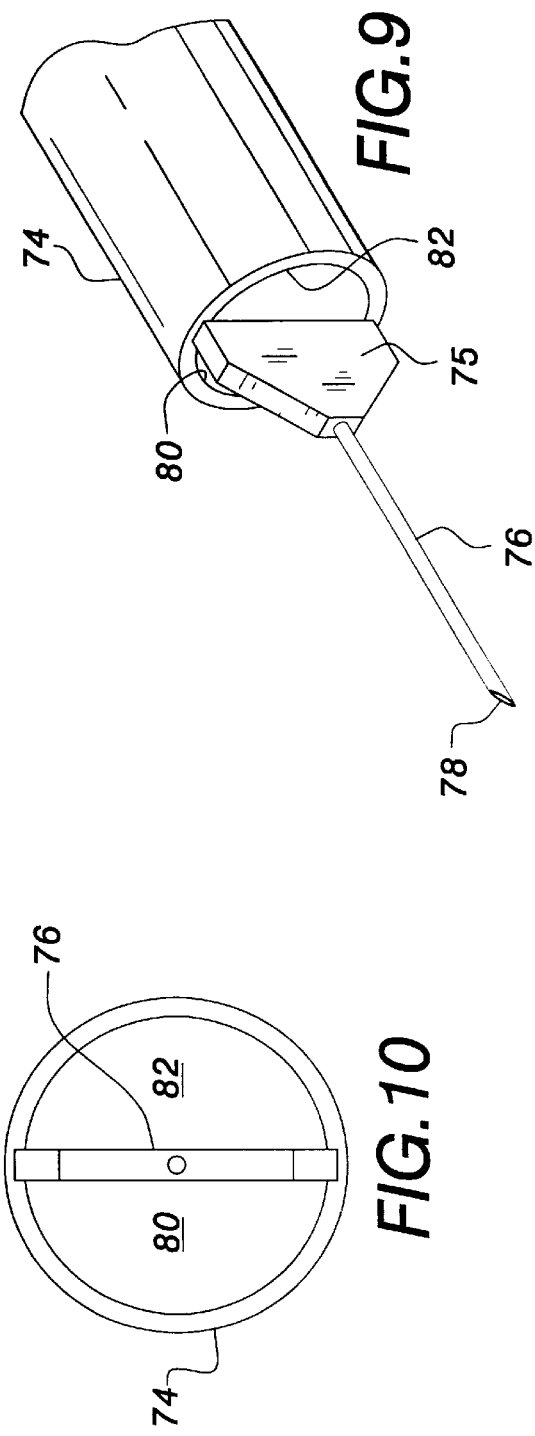

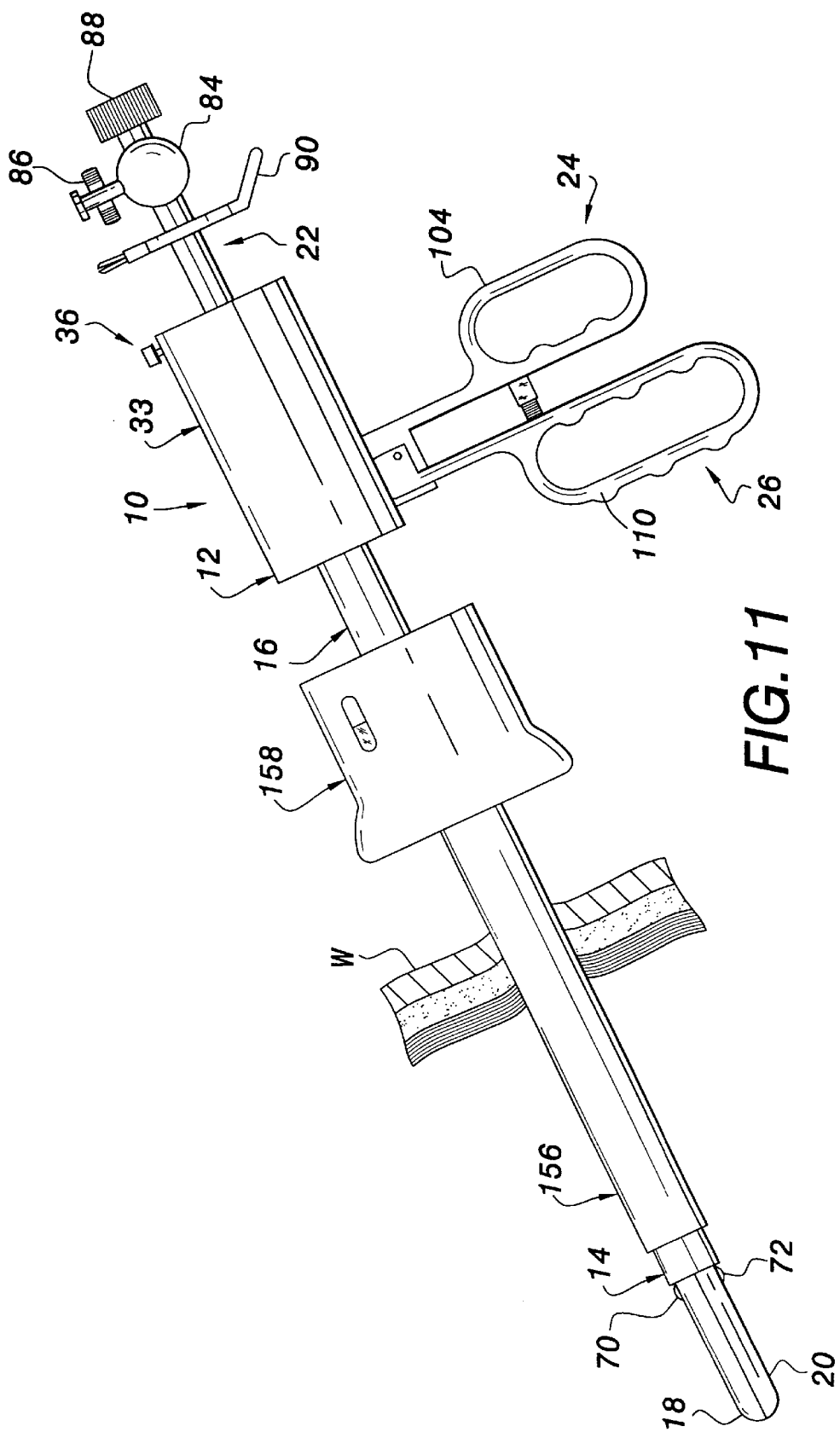

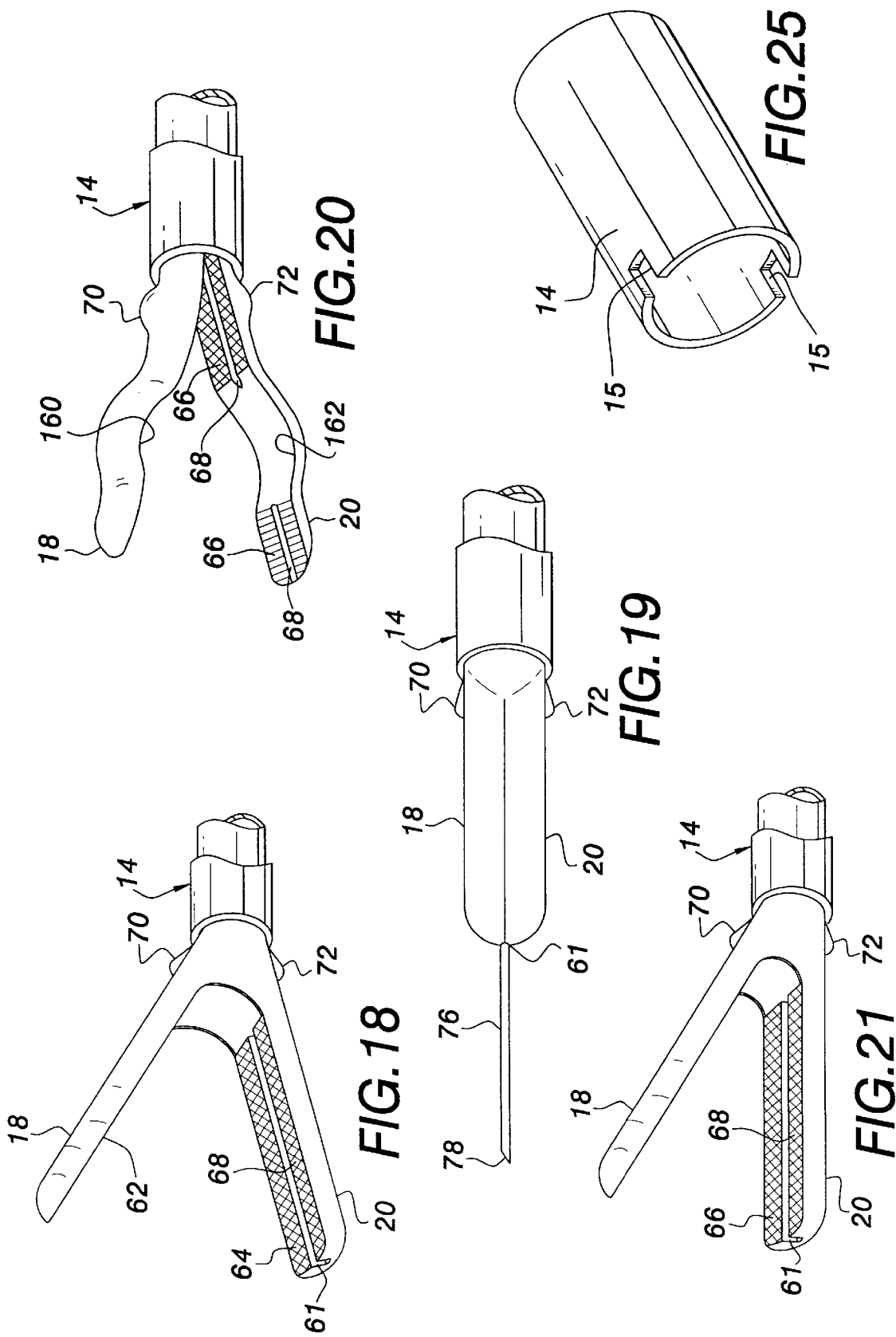

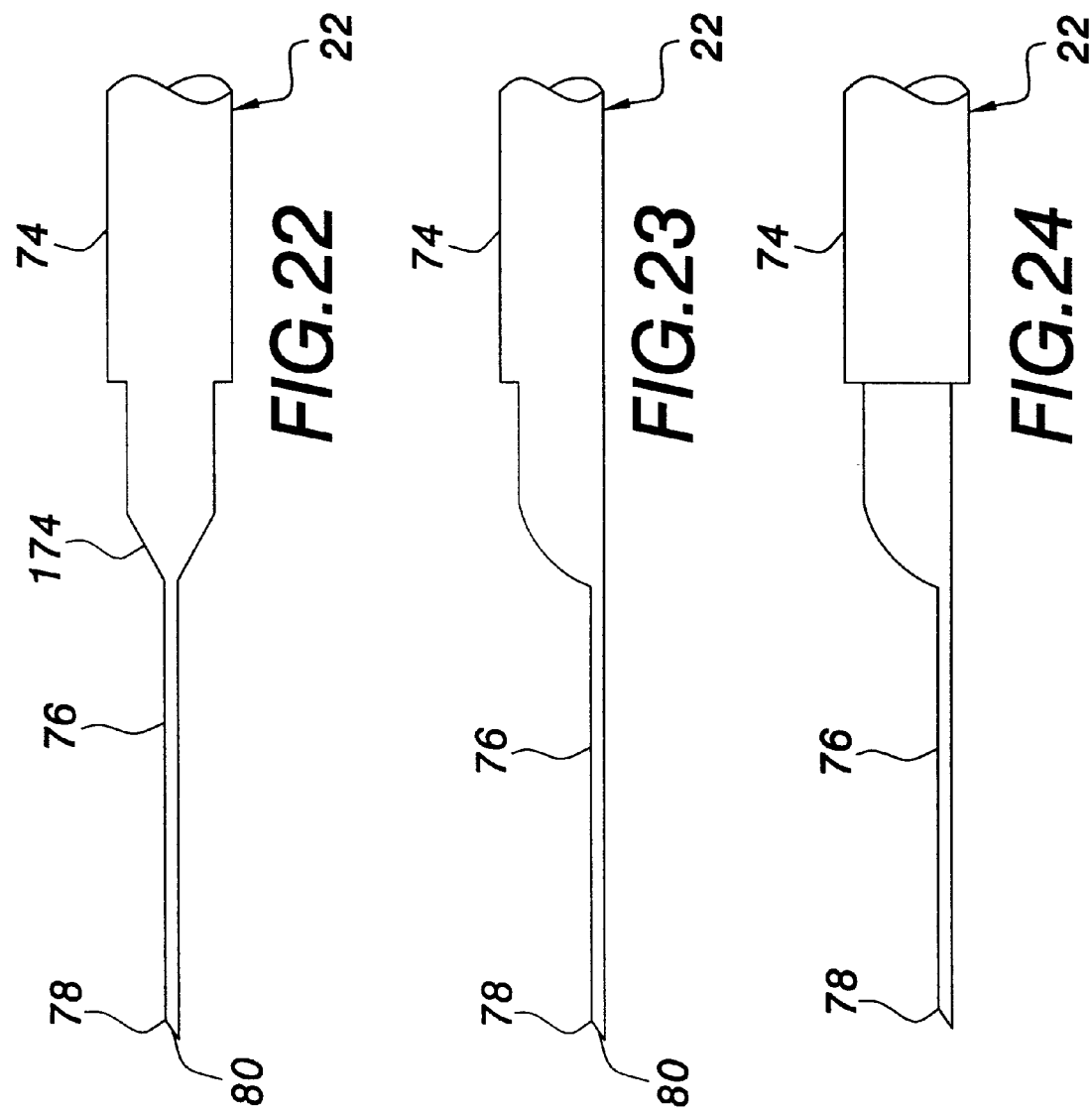

SURGICAL INSTRUMENT WITH JAWS AND MOVABLE INTERNAL NEEDLE AND METHOD FOR USE THEREOF

CROSS-REFERENCE TO RELATED APPLICATIONS

This application is a continuation-in-part of Ser. No. 08/376,186, filed on Jan. 20, 1995, now U.S. Pat. No. 5,665,100, which is a continuation-in-part of applicant's copending patent application Ser. No. 08/281,814, filed Jul. 28, 1994, abandoned, which is a continuation of patent application Ser. No. 08/073,193, filed Jun. 8, 1993, now U.S. Pat. No. 5,334,209, which is a continuation of patent application Ser. No. 07/720,381, filed Jun. 25, 1991, now U.S. Pat. No. 5,217,473, which is a divisional of patent application Ser. No. 07/446,555, filed Dec. 5, 1989, now U.S. Pat. No. 5,026,379, the disclosures of which are incorporated herein by reference.

BACKGROUND OF THE INVENTION

1. Field of the Invention

The present invention relates generally to medical procedures and instruments and, more particularly, to a multifunctional instrument having jaws, a central channel, and a moveable needle disposed in the channel for performing endoscopic procedures.

2. Discussion of the Related Art

Endoscopic and minimally invasive medical procedures, such as laparoscopy, have become widely accepted for surgery and diagnosis due to the associated advantages relating to reduced trauma and hospitalization time. The performance of an endoscopic procedure typically involves creation of one or more puncture sites through a wall of an anatomical cavity using a penetrating instrument including an obturator, such as a trocar, disposed within a portal sleeve. After the penetrating instrument has penetrated into the anatomical cavity, the obturator is withdrawn leaving the sleeve in place to form a portal in the cavity wall for the introduction of instruments such as endoscopes, ligating appliers, forceps, cauteries and the like into the anatomical cavity.

Endoscopic procedures commonly involve performing a number of individual acts or functions within the anatomical cavity including grasping, cutting, coagulating, irrigating, aspirating, puncturing, injecting, dissecting, cauterizing, ligating, suturing, illuminating, visualizing and/or collecting specimens for biopsy. However, typical endoscopic instruments are capable of performing at most two of the above functions, requiring several incisions for placement of multiple portal sleeves to accommodate a suitable number of endoscopic instruments for performing the required functions or necessitating frequent withdrawal and replacement of individual endoscopic instruments through a single incision. While it is generally desirable to minimize the number of incisions created for performing a particular endoscopic procedure, substitution of instruments through a single incision can be time consuming, depending on the efficiency of the medical facility and staff, increasing the period of anesthetization for the patient. Additionally, internal bleeding can develop during the substitution of instruments thereby obscuring the field of view and requiring time consuming cleanup procedures to be performed.

A disadvantage of endoscopic instruments having articulated jaws, in particular, is that the jaws are typically mounted on pivots at the distal end of relatively long shafts requiring complicated and space-consuming linkages for converting the user's proximal movements into motion of the jaws and increasing the risk of fluid leaking through poorly sealed pivotal mounts.

SUMMARY OF THE INVENTION

Accordingly, it is a primary object of the present invention to overcome the above mentioned disadvantages of the prior art with an endoscopic instrument capable of performing multiple functions.

Another object of the present invention is to minimize the number of incisions required for performing an endoscopic procedure by performing multiple functions through a single incision with an endoscopic instrument having a forceps unit with jaws for performing grasping functions, a channel formed through the forceps unit, and a movable inner member having a needle disposed in the channel for performing at least one of the functions of grasping, cutting, dissecting, aspirating, irrigating, penetrating, injecting, creating suction, collecting biopsy samples, hooking, manipulating and cauterizing through the forceps unit.

It is another object of the present invention to lock jaws of an endoscopic instrument together to ensure smooth entry of the endoscopic instrument through a portal sleeve and to prevent inadvertent snagging of anatomical tissue.

Some of the advantages of the present invention over the prior art are that the endoscopic instrument can perform multiple functions through a single incision thereby minimizing the number of incisions required to perform an endoscopic procedure, that use of an endoscopic instrument for picking-up and holding objects is simplified, that objects can be held without the need for exerting continuous hand or finger pressure, that single-handed operation of a forceps unit and a needle is facilitated, that conventional handle structures can be used to provide the surgeon with a familiar feel and to decrease adaptation time, that the instrument can be fabricated at low cost using simple mechanisms without complicated linkages, and that the instrument can be sterilized for reuse or disposable for single patient use as desired.

The present invention is generally characterized in an endoscopic instrument including a forceps unit for being positioned within an anatomical cavity and a moveable inner member having a needle disposed in a channel formed through the forceps unit. The forceps unit includes a housing, a tubular outer member, an intermediate member, and a handle mechanism coupled with at least one of the intermediate and outer members for creating relative movement therebetween. The outer member has a proximal end mounted on the housing and terminates distally at a distal end. The intermediate member has a tubular body disposed telescopically within the outer tubular member, a proximal end mounted in the housing and an integral one-piece distal end defining a pair of opposed jaws resiliently biased apart such that relative movement of the outer tubular member distal end over the jaws causes the jaws to close. The movable inner member is disposed at least partly within the intermediate member and has a needle disposed on a distal end for performing at least one of the functions of hooking, manipulating, dissecting, collecting tissue for biopsy, penetrating, injecting, creating suction, aspirating, irrigating and cauterizing.

A further aspect of the present invention is generally characterized in a method of performing an endoscopic procedure including the steps of introducing a tubular member with integral one-piece jaws through an opening in an anatomical cavity wall, grasping anatomical tissue with the jaws, advancing a moveable inner member having a needle distally through the tubular member, and performing a medical procedure involving at least one of the functions of dissecting, cauterizing, penetrating, injecting, hooking, manipulating, collecting a biopsy, irrigating and aspirating with the inner member.

Yet another aspect of the present invention is generally characterized in a method of performing endoscopic procedures including the steps of introducing a tubular member with jaws through an opening in an anatomical cavity wall, advancing an inner member having a needle distally through the tubular member until the needle protrudes distally from the jaws and performing a medical procedure with the needle.

Other objects and advantages of the present invention will become apparent from the following description of the preferred embodiments taken in conjunction with the accompanying drawings, wherein like parts in each of the several figures are identified by the same reference characters.

BRIEF DESCRIPTION OF THE DRAWINGS

FIG. 3 illustrates the intermediate member removed from the outer member for clarity.

FIG. 4 illustrates one of the jaws of the preferred embodiment;

FIG. 5 illustrates the jaw of FIG. 4 taken in section along line 5—5;

FIG. 6 illustrates the other jaw of the preferred embodiment;

FIG. 7 illustrates the jaw of FIG. 6 taken in section along line 6—6;

FIG. 8 illustrates the inner member removed from the outer member and intermediate member for clarity;

FIG. 9 is a perspective view of the distal end of the inner member;

FIG. 10 is a frontal view of the inner member as viewed distally;

FIG. 11 illustrates the preferred embodiment in use;

FIG. 18 illustrates a modified jaw configuration;

FIG. 19 illustrates a modified jaw configuration;

FIG. 20 illustrates a modified jaw configuration;

FIG. 21 illustrates a modified jaw configuration;

FIG. 22 illustrates a modified inner member;

FIG. 23 illustrates a modified inner member;

FIG. 24 illustrates a modified inner member;

FIG. 25 illustrates a distal end of a modified outer member.

DETAILED DESCRIPTION OF THE PREFERRED EMBODIMENT

The endoscopic instrument of the present invention can be utilized in any type of anatomical cavity. Therefore, while the instrument is described hereinafter for use with a portal sleeve in endoscopic procedures, such as laparoscopy, the instrument can be used with catheters and other small and large diameter cylindrical members providing access to small cavities, such as veins and arteries, as well as large cavities, such as the abdomen.

Figure 1:
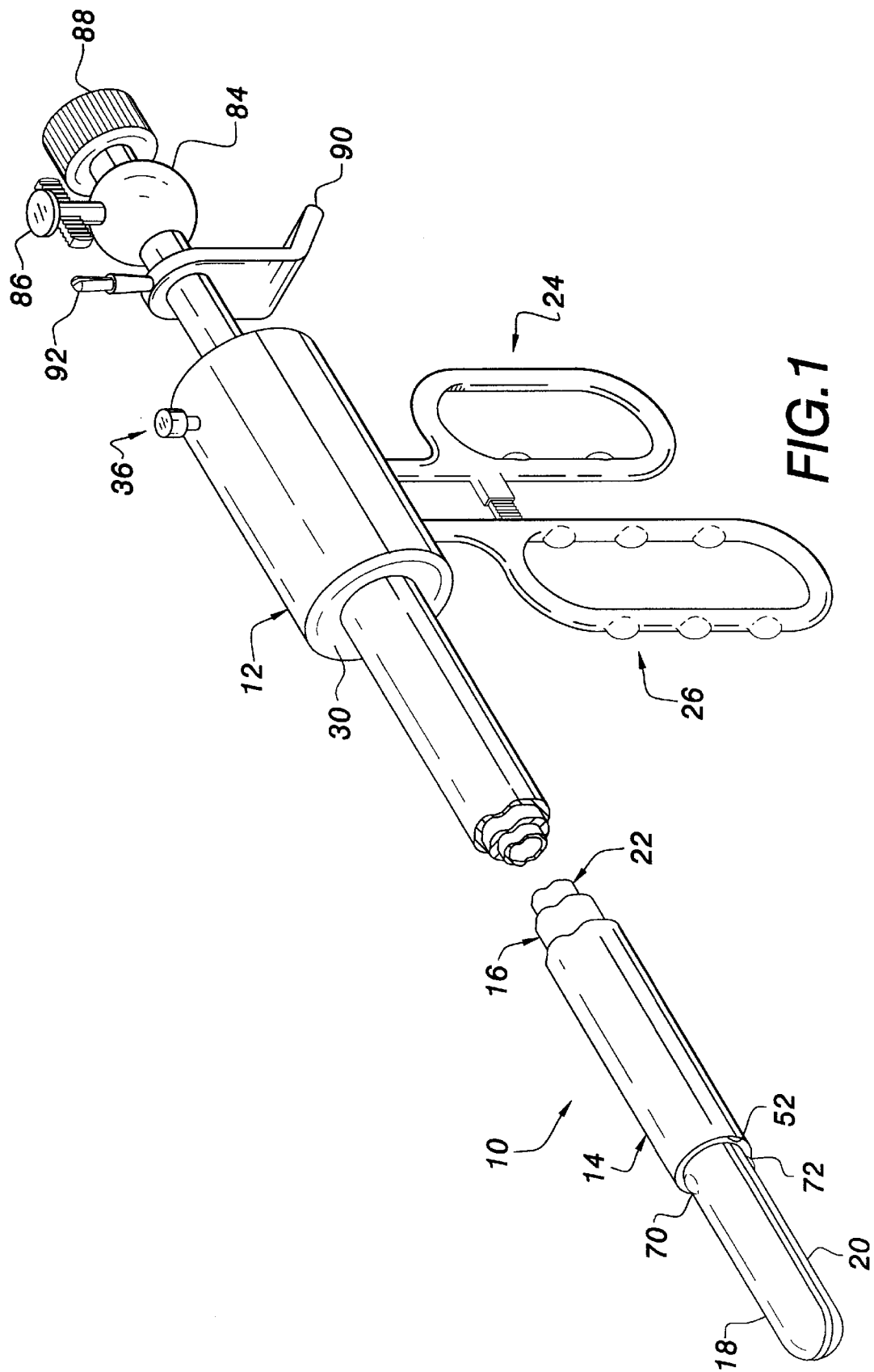
FIG. 1 is a perspective view, broken longitudinally, of an endoscopic instrument according to a preferred embodiment of the present invention.

Endoscopic instrument 10 according to a first preferred embodiment of the present invention, as shown in FIG. 1, includes housing 12, tubular outer member 14 extending distally from housing 12, tubular intermediate member 16 telescopically fitted within outer tubular member 14 and having opposed jaws 18 and 20 on a distal end thereof, fixed handle 24 and movable handle 26 extending from housing 12 and inner member 22 which is at least partly telescopically fitted within intermediate member 16.

Figure 2:
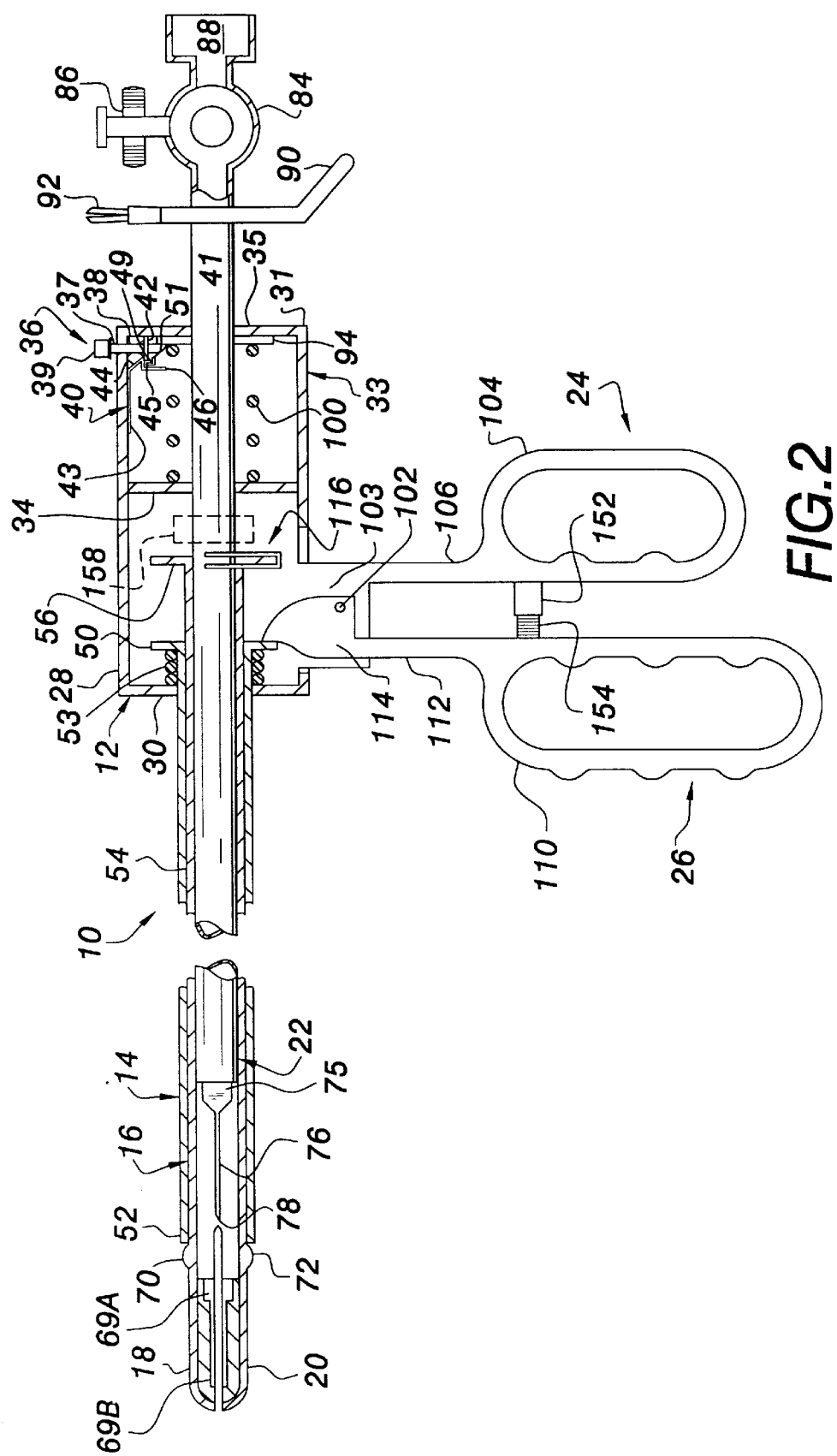
FIG. 2 is a sectional view of the preferred embodiment.

As shown in FIG. 2, housing 12 is generally tubular with cylindrical sidewall 28, front and rear walls 30 and 31 closing opposite ends of cylindrical sidewall 28 and intermediate wall 34 dividing housing 12 into two compartments. Slotted opening 48 is formed in cylindrical sidewall 28 of housing 12 and extends longitudinally between wall 30 and intermediate wall 34 to permit movable handle 26 to pass therethrough. Fixed handle 24 extends from plate 103 formed on housing 12 proximate slot 48. Plate 103 can be formed integrally with housing 12 or can be fixedly attached to housing 12 to be stationary relative thereto.

Outer member 14 is open at both ends and extends through an opening in front wall 30 to terminate proximally at transverse flange 50 disposed between front wall 30 and intermediate wall 34 of housing 12 (see FIG. 2). Distal end 52 of outer tubular member 14 can be blunt as shown, tapered, beveled or chamfered as desired or have any other suitable distal configuration. Preferably, outer member 14 is made of a substantially cylindrical length of a substantially rigid material, such as stainless steel or other medically acceptable plastic or metal material.

Intermediate member 16 includes tubular body 54 telescopically fitted within outer member 14. Tubular body 54 terminates proximally at transverse flange 56 disposed within housing 12 between the outer tubular member flange 50 and intermediate wall 34 and, as is best seen in FIGS. 3–7 which show intermediate member 16 removed from outer member 14 for illustrative purposes, a distal end of tubular body 54 is split longitudinally to form integral one-piece jaws 18 and 20 that oppose one another. Jaws 18 and 20 are normally biased apart as shown and define opposed semicylindrical recesses 58 and 60 (see FIGS. 5 and 7) for carrying jaw inserts 62 and 64 respectively.

Jaw inserts 62 and 64 can be permanently or removably secured within semicylindrical recesses 58 and 60 using adhesives, detents, or any other suitable method of attachment or can be formed with jaws 18 and 20 as an integral one-piece construction. Each of inserts 62 and 64 defines grasping surface or tread 66 suitable for grasping anatomical tissue, or holding instruments such as a needle, and longitudinal groove 68 extending from a proximal end of the insert to a position proximally spaced from the distal end of the insert. Groove 68 has deep portion 69a and shallow portion 69b. A repeated pattern of diamond-shaped protrusions is shown for tread 66. However, other surfaces such as those having parallel ribs or textured portions could be used. The depth of each groove 68 will depend on the size of a needle carried by the inner member 22 as will be described in more detail below. Wedge-like cams 70 and 72 are formed on respective exterior surfaces of jaws 18 and 20 and are distally spaced from outer member distal end 52 when jaws 18 and 20 are open. Cams 70 and 72 taper toward the joint region or junction where each jaw connects with tubular body 54.

As best seen in FIG. 3, tubular body 54 of intermediate member 16 is preferably formed with jaws 18 and 20 as a single unitary part using a resilient medically-acceptable material such as a spring steel or plastic having suitable elastic properties for normally biasing the upper and lower jaws 18 and 20 apart while permitting jaws 18 and 20 to be moved towards one another in response to axial forces acting on the jaws and/or cams as a result of relative movement between outer tubular member 14 and intermediate member 16. Referring again to FIG. 2, it can be seen that bias member 53 is connected between outer member flange 50 and front wall 30 such that outer member 14 is normally biased in a proximal direction relative to intermediate member 16. Bias member 53 is shown as a helical coil spring disposed around intermediate member 16 and held in compression between the outer member flange 50 and front wall 30. However, bias member 53 can be constituted of various other types of springs as well as other types of bias devices including tension springs, torsion springs, pan springs, leaf springs, rubber, plastic or magnets, for example.

As best seen in FIGS. 8–10 which illustrate inner member 22 removed from outer member 14 and intermediate member 16 for illustrative purposes, inner member 22 includes tubular shaft 74 which terminates distally at open end 73 carrying an operating member in the form of coaxial needle 76 with distal tissue-penetrating tip 78 and proximal flat plate-like base 75 arranged diametrically across open distal end 73 of tubular shaft 74. Base 75 is sized to slidably fit in deep portion 69a of grooves 68. Referring to FIG. 2, tubular shaft 74 is telescopically fitted within the tubular portion of intermediate member 16 and extends through aligned openings in the front and rear walls 30 and 31 and intermediate wall 34 of housing 12 to terminate proximally outside housing 12 at spherical reservoir 84 with a proximal aperture 88 and a stop cock valve 86 disposed within reservoir 84 for controlling passage of instruments and/or fluids through the aperture and into tubular shaft 74.

Handle 90 extends transversely from tubular shaft 74 near the proximal end of tubular shaft 74 and is angled proximally to form a finger rest. Insulated connector 92 can be provided to permit electrical conductors to enter the tubular shaft 74 on a side opposite handle 90 to be connected with electrically conductive elements of instrument 10 for performing unipolar or bipolar electric coagulation, for example using needle 76 or jaws 18 and 20 as a conductive element. Tubular shaft 74 also carries transverse flange 94 disposed within housing 12 between rear wall 31 and intermediate wall 34 (see FIG. 2). Bias member 100, shown as a helical coil spring, is disposed around tubular shaft 74 and held in compression between flange 94 and intermediate wall 34 to bias inner member 22 proximally within housing 12 and intermediate member 16.

Inner member 22 is prevented from being inadvertently moved in a distal direction by a safety mechanism 36, similar to that disclosed in the parent application, disposed within housing 12 as shown in FIG. 2. A push-button type of safety mechanism 36 is shown whereby inner tubular member 22 can be locked in a retracted position with flange 94 abutting rear wall 31 by depressing button 39 and can subsequently be released prior to being moved distally by depressing button 39 a second time. It will be appreciated, however, that other safety mechanisms can be used, including rotatable levers, detents, and splined collars for example. Safety mechanism 36 includes post 37 extending radially through housing 12, bias member 38 connected between post 37 and housing 12 for biasing post 37 radially outward, push-button 39 mounted on top of post 37 externally of housing 12 latch spring 40 disposed within housing 12 for engaging post 37 in a locked position where a lower end of post 37 engages flange 94, and trigger 41 for releasing latch spring 40 to allow post 37 to move radially outward to an unlocked position.

Post 37 is oriented transversely relative to the longitudinal axis of inner member 22 and includes annular flange 42 disposed within housing 12. Bias member 38 is shown as a helical coil spring disposed around post 37 and held in tension between housing 12 and annular flange 42 to bias post 37 radially outward of housing 12. Latch spring 40 is formed of a resilient strip of material configured to have flat base 43 secured to an outer wall of the hub and downwardly angled arm 44 extending from a proximal end of base 43 toward the post 37. Arm 44 bends back on itself to form latching surface 45 that is substantially parallel annular flange 42. Transverse extension 46 of arm 44 extends from a distal end of latching surface 45 in parallel to the post 37. Trigger 41 is disposed proximate arm extension 46 and is pivotally mounted in housing 12. Trigger 41 is generally L-shaped and has leg 49 overlying arm extension 46 and leg 51 extending transversely from leg 49 and at a slight downward angle, to be disposed beneath annular flange 42 when post 37 is in the locked position shown in FIG. 2. A torsion spring (not shown) can be connected between trigger 41 and housing 12 to bias trigger 41 in a counterclockwise direction in FIG. 2 such that leg 49 is normally in contact with the arm extension 46.

Referring still to FIG. 2, it will be seen that movable handle 26 is pivotally mounted on pin 102 which is secured to plate 103 which extends outward from side wall 28 along an edge of slotted opening 48. Fixed handle 24 includes finger loop 104 configured to accommodate one or more fingers, or the thumb, of the surgeon and shank 106 connecting finger loop 104 with mounting plate 103. Movable handle 26 includes finger loop 110 configured to accommodate one or more fingers of the surgeon and shank 112 connecting finger loop 110 with flattened end portion 114 which extends into housing 12 towards flange 50 of outer member 14 through slotted opening 48. Flange 56 of intermediate member 16 is fixed to housing 12 by bracket 116. Therefore, when the surgeon squeezes finger loop 110 towards finger loop 104, handle 26 pivots about pin 102 and flattened portion 114 presses flange 50 distally. This causes distal end 52 to move at least partly over flanges 70 and 72 thus closing jaws 18 and 20.

A pair of mating protrusions 152 and 154 are carried at opposed locations on finger loops 104 and 110 respectively to lock handles 24 and 26 together when pressed towards one another a predetermined angular distance corresponding to a desired resultant position of jaws 18 and 20. Mating protrusions 152 and 154 are shown having serrated inside surfaces, but can have any other configuration to ratchet, mate frictionally and/or latch together when engaged.

Use of endoscopic instrument 10 of the present invention is illustrated in FIGS. 11–17, wherein instrument 10 is shown being guided through portal sleeve 156 positioned in wall W of an anatomical cavity. Instrument 10 is preferably passed through portal sleeve 156 with jaws 18 and 20 at least partly closed so that instrument 10 can be inserted without catching on anatomical tissue or snagging structure within portal sleeve 156. Since outer member 14 can be held by protrusions 152 and 154 in a position partly closing jaws 18 and 20, the surgeon need not exert any force on handles 24 and 26 of instrument 10 during insertion.

With jaws 18 and 20 partly closed, endoscopic instrument 10 is inserted through portal sleeve 156 positioned within the anatomical cavity wall W, as shown in FIG. 11, to access an operative site within the anatomical cavity. Portal sleeve 156 can be positioned in the wall using any suitable penetrating technique, including those creating puncture sites by means of removable obturators such as trocars, and is shown carrying valve housing 158 at a proximal end to prevent the loss of pneumoperitoneum during insertion and withdrawal of endoscopic instrument 10. Visualization of the endoscopic procedure can be accomplished using a conventional endoscope (not shown) incorporated into endoscopic instrument 10, for example within tubular shaft 74, or separately positioned within the anatomical cavity through a second portal sleeve located at another puncture site.

Figure 12:
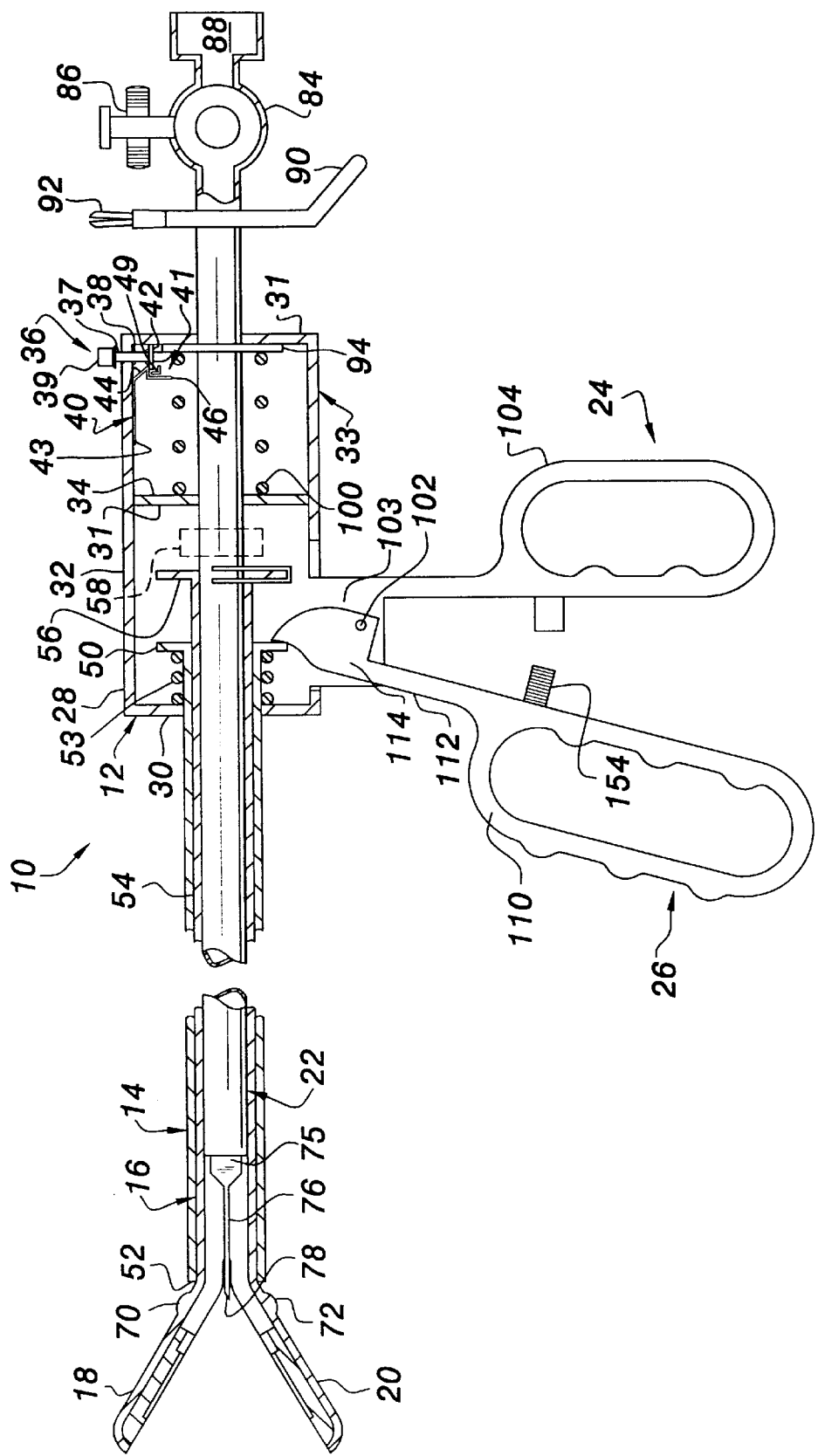
FIG. 12 is a sectional view of the preferred embodiment with the jaws open.

Endoscopic instrument 10 is advanced distally through portal sleeve 156 until jaws 18 and 20 emerge into the anatomical cavity. At this point, jaws 18 and 20 can be opened to permit visualization by an endoscope through tubular shaft 74 or can remain closed in the case of using a separately positioned endoscope. If jaws 18 and 20 are to be opened, this is accomplished by exerting finger pressure on finger loops 104 and 110 to release protrusion 152 and 154 to spread the loops apart, as shown in FIG. 12, due to the force of biasing member 53. Pivotal movement of finger loop 110 about pin 102 permits flange 50 to move proximally with respect to intermediate member 16 due to the force of biasing member 53. This causes distal end 52 of outer member 14 to slide off cams 52 and 72 in a proximal direction allowing jaws 18 and 20 to spread apart elastically.

Figure 13:
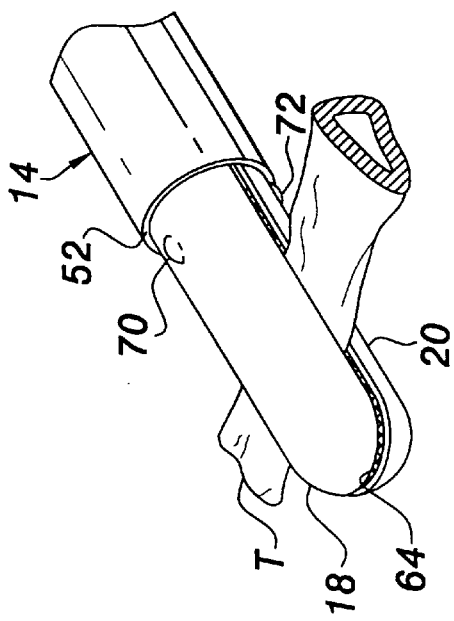
FIG. 13 illustrates the jaws of the preferred embodiment with tissue positioned therebetween.

Instrument 10 can be moved within the anatomical cavity with jaws 18 and 20 in either the open or closed condition depending on the type of visualization utilized and the desirability of presenting a narrow or wide jaw profile during movement. In FIG. 13, jaws 18 and 20 are shown in the opened condition for being positioned around anatomical tissue T to be grasped. Tissue T is located between tissue grasping inserts 62 and 64 so that when jaws 18 and 20 are partly closed, for example by placing finger pressure on the handles 24 and 26 to close jaws 18 and 20, tissue T will be held securely within the small gap between the jaws 18 and 20 as shown in FIG. 14.

Figure 14:
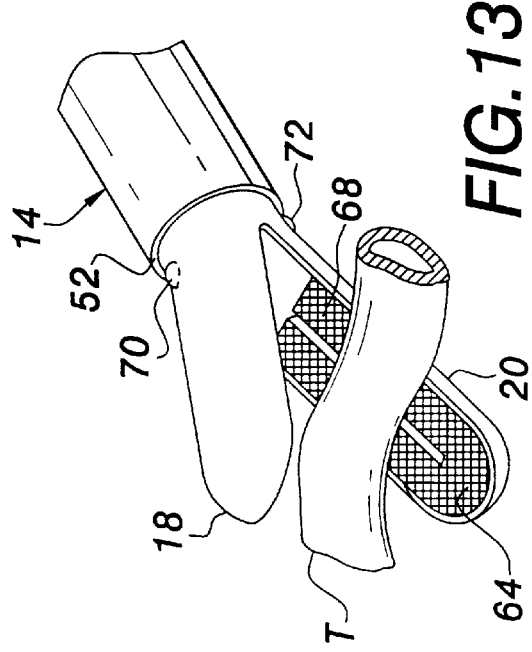
FIG. 14 illustrates the jaws of the preferred embodiment grasping tissue.
Figure 15:
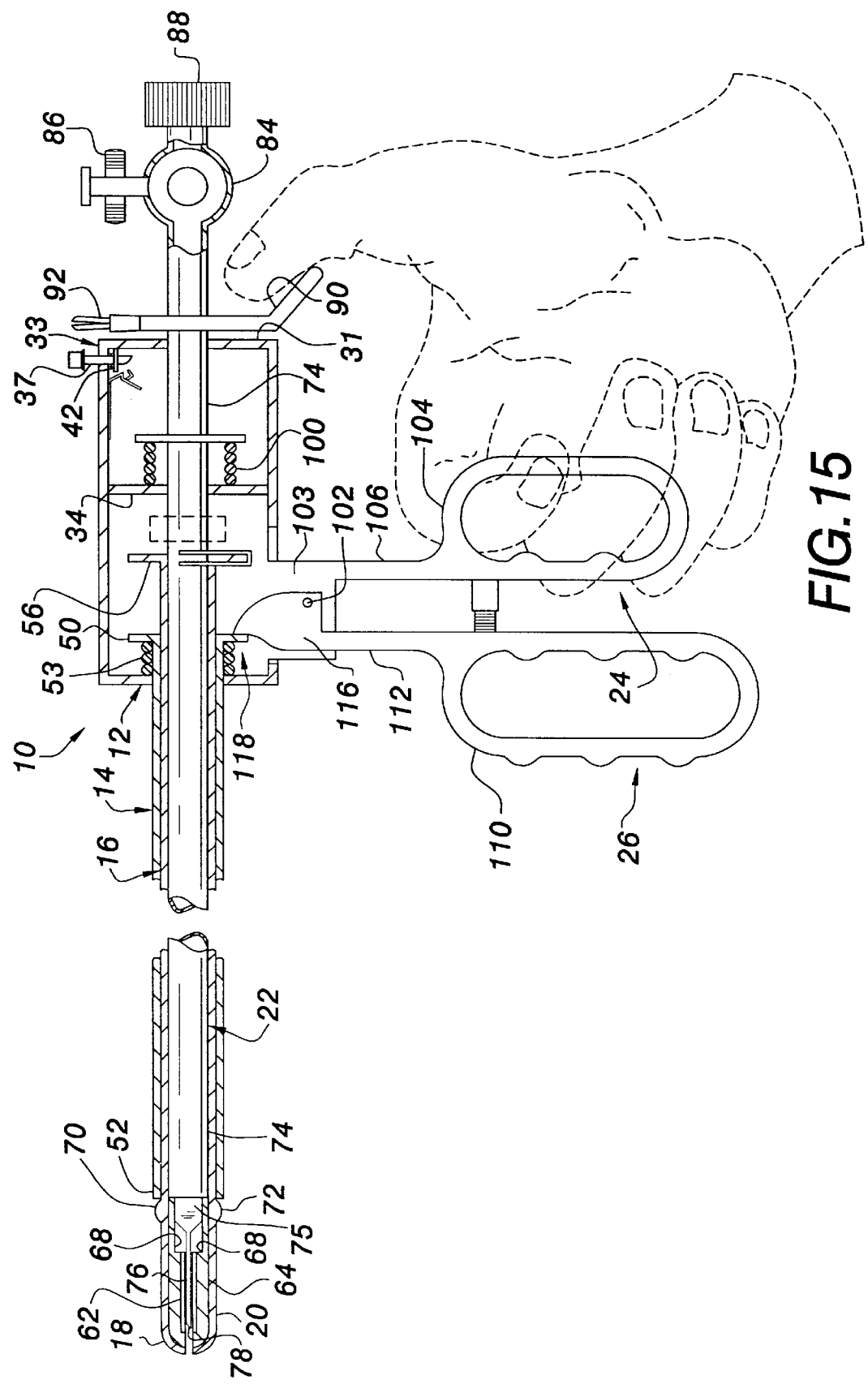
FIG. 15 is a sectional view of the preferred embodiment with the inner member advanced into the jaws.

With tissue T firmly grasped between jaws 18 and 20 as illustrated in FIG. 14, inner member 22 can be advanced distally as shown in FIG. 15 to move base 75 along insert grooves 68 thereby piercing anatomical tissue T held between the jaws with needle 76 (tissue T is omitted in FIG. 15 for clarity). First, safety mechanism 36 is released by pressing down on push-button 39 to cause annular flange 42 formed on post 37 to engage trigger leg 51 rotating the trigger clockwise in FIG. 2. Trigger 41 is spring-biased in a counterclockwise direction and will thus return to its original position once annular flange 42 advances beyond trigger leg 51. When pressure on the push-button 39 is released, safety bias member 38 will draw the post 37 upward in FIG. 2 so that the flange 42 will engage trigger leg 51 from the other side causing the trigger 41 to rotate counterclockwise and trigger leg 49 to bear against arm extension 46. Arm extension 46, and thus latching surface 45, are moved away from the post permitting bias member 38 to move the post to its unlocked position shown in FIG. 15 where flange 42 abuts wall 28.

With safety 39 mechanism disabled, inner member 22 can be advanced by moving handle 90 toward housing 12. Needle 76 at the distal end of the inner member 22 is slidable into the space defined between jaws 18 and 20 to pierce any tissue held between jaws 18 and 20. Since deep portions 69a of grooves 68 in this embodiment do not extend the entire length of jaws 18, the distal ends of the deep portions 69a can also serve as stops or abutments limiting the distal movement of plate 75 and thus needle 76 when jaws 18 and 20 are closed to protect surrounding organ structures. As mentioned previously, tubular shaft 74 is hollow and can thus be utilized for creating suction during the procedure, performing aspiration or irrigation or to facilitate passage of additional instruments or fluids into the anatomical cavity as desired. After a piercing procedure, needle 76 can be retracted under the influence of bias member 100 or jaws 18 and 20 can be opened to release tissue T and instrument 10 can be manually withdrawn.

Figure 16:
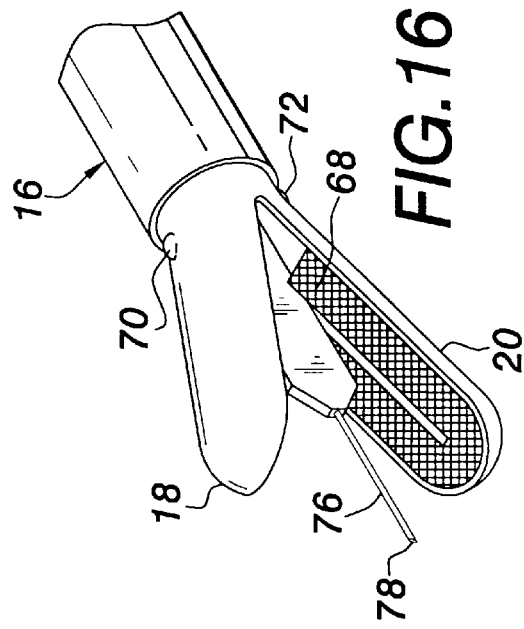
FIG. 16 illustrates the jaws of the preferred embodiment in an open position with the needle at the inner member advanced.

Piercing can be accomplished without grasping using endoscopic instrument 10 in the manner illustrated in FIG. 16. Use of instrument 10 in this manner proceeds essentially as described above for a grasping and piercing procedure. However, inner member 22 is moved distally with jaws 18 and 20 in the open condition. With needle 76 exposed, instrument 10 can then be advanced against anatomical tissue or other objects and suitably manipulated to pierce or puncture the tissue or objects to a desirable depth. Needle 76 can be locked in the extended position shown or any other position relative to housing 12 by use of additional safety mechanisms, like that of safety mechanism 36, or any other type of known locking mechanisms.

Figure 17:
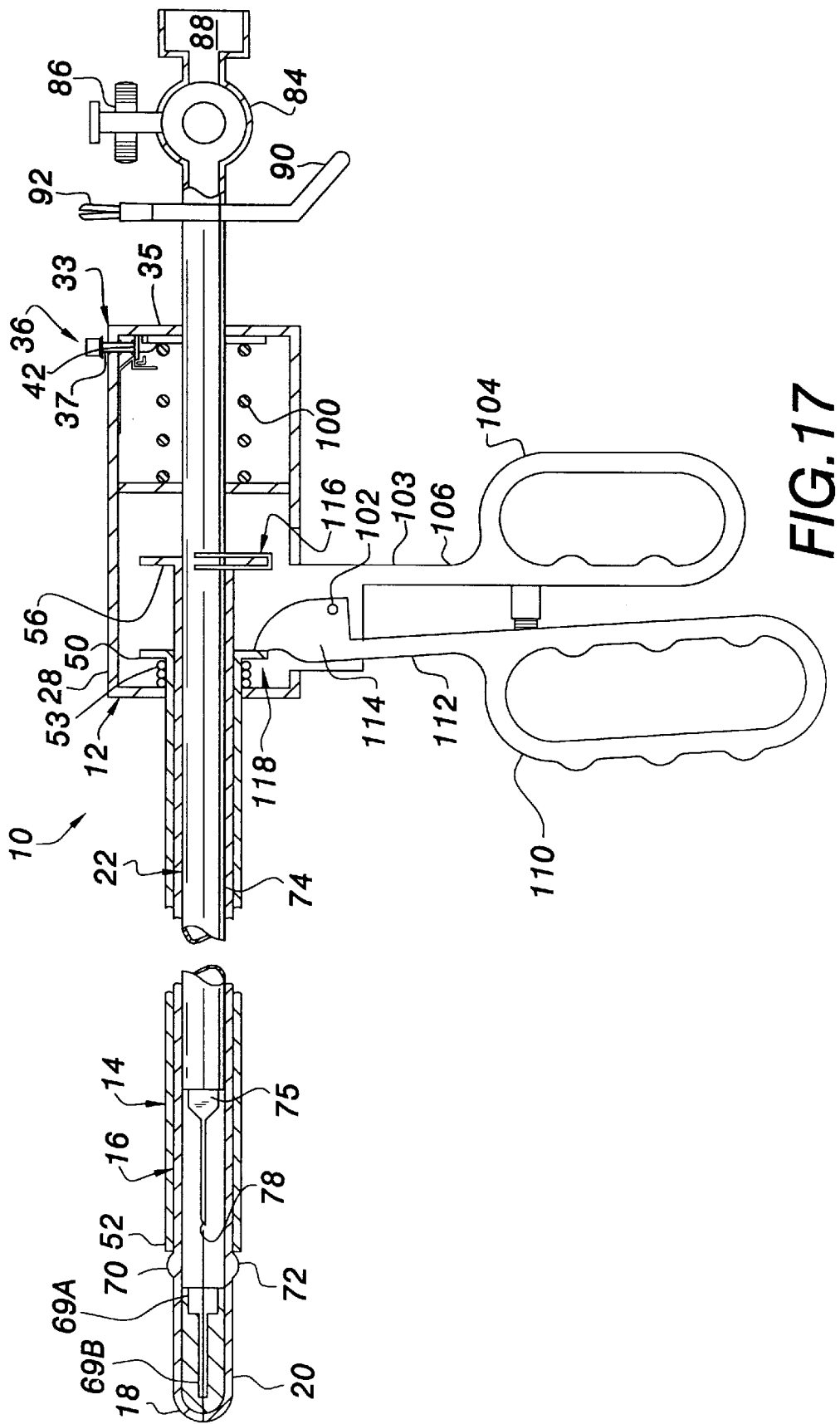
FIG. 17 is a sectional view of the preferred embodiment with the jaw pressed tightly closed.

As mentioned previously, tissue can be grasped and securely held with jaws 18 and 20 in a partly closed state. However, for certain procedures it may be desirable to draw jaws 18 and 20 completely together as shown in FIG. 17, with or without objects held between the jaws. Jaws 18 and 20 can be closed completely or clamped together by drawing finger loops 104 and 110 towards one another until distal end 52 of outer member 14 slides distally over cams 70 and 72 to force jaws 18 and 20 into close contact with one another. If tissue or some other object is disposed between jaws 18 and 20, advancement of outer member 14 over cams 70 and 72 will result in greater compression of the object. When finger loops 104 and 110 are drawn sufficiently close to one another, mating protrusions 152 and 154 will be engaged, locking handles 24 and 26 in their current position. If mating protrusions 152 and 154 are ratcheted as shown, various degrees of compression can be achieved and maintained without continuous finger pressure being applied. With jaws 18 and 20 entirely closed, needle 76 can be advanced into the space defined by shallow portions 69b of grooves 68.

A modification of endoscopic instrument 10 of the preferred embodiment is illustrated in FIGS. 18 and 19 wherein jaws 18 and 20 and tissue grasping jaw inserts 62 and 64 are formed as an integral one-piece unit and grooves 68 are made to extend along the entire length of the tissue grasping inserts 62 and 64 to define an aperture 158 at the distal end of jaws 18 and 20 when jaws 18 and 20 are closed. Aperture 61 can be used for permitting needle 76 to extend distally beyond jaws 18 and 20 or for permitting passage of other operating members through jaws 18 and 20 when closed, as illustrated in FIG. 19. Of course, this embodiment can have shallow portion 69b and deep portion 69a formed in groove 68 in an appropriate manner.

FIG. 20 shows a further modification of the endoscopic instrument 10 of the present invention in which jaws 18 and 20 include arcuate or concave portions 160 and 162, respectively, integrally-formed at opposed locations along the length of jaws 18 and 20. Arcuate portions 160 and 162 cooperate to define a substantially circular transverse passage through jaws 18 and 20 when closed and can thus hold a tubular organ, other anatomical tissue or an object therebetween for being manipulated or pierced without compressing or flattening the organ, tissue or object. Tissue gripping surfaces 66 are formed on the flat portions of jaws 18 and 20 and can be formed along arcuate portions 160 and 162 as well. Grooves 68 are interrupted by arcuate portions 160 and 162 but extend longitudinally along flat portions of jaws 18 and 20 and are aligned to form a track for guiding plate 75 and needle 76 across arcuate portions 160 and 162. When grooves 68 extend the entire length of jaws 18 and 20 as shown, grooves 68 can define an aperture such as aperture 61 at the distal end of jaws 18 and 20. This modification also can have deep portions 69a and shallow portions 69b as needed.

In yet another modification of the endoscopic instrument 10 of the preferred embodiment shown in FIG. 21, lower jaw 20 is fixed and extends distally from tubular body 54 along a longitudinal axis of tubular body 54. Upper jaw 18 in FIG. 21 has cam 70 and is movable from an open position normally extending at an angle relative to the longitudinal axis of tubular body 54 to a closed position where it mates with fixed lower jaw 20. Fixed lower jaw 20 can also carry a cam 72. Jaws 18 and 20 include tissue gripping surfaces 66 and grooves 68 formed along the length of the tissue gripping surfaces to serve as a guide for needle 76 and to form a distal aperture similar to aperture 61 shown in FIG. 19.

Fluids can be introduced or drawn through tubular shaft 74 via open distal end 73; and in the case of fluid introduction, the presence of the flat base 175 across the opening will tend to separate any fluid flow for increased dispersion.

Other modified inner members 22 can be used also. Inner member 22 shown in FIG. 22 is similar to that shown in FIGS. 8, and 18–20 except it has tubular shaft 74 terminating distally in an inwardly tapered frustoconical portion 174 carrying coaxial needle 76 with sharp tissue-penetrating tip 78. Needle 76 is hollow and has a beveled opening 80 at a distal end for allowing passage of fluids. The peripheral edge of beveled opening 80 defines a sharp tissue-penetrating tip 78 of needle protrusion 76 and can be used for penetrating anatomical tissue held between jaws 18 and 20 or can be protruded distally from aperture 61 when jaws 18 and 20 are closed. Various fluids can be precisely administered or extracted from the anatomical tissue or cavity using hollow needle 76 with valve 86 opened and proximal aperture 88 connected with appropriate instrumentation such as suction lines, fluid sources or any other fluid handling apparatus.

The inner member distal configurations shown in FIGS. 23 and 24 are similar to those illustrated in FIGS. 8 and 22, respectively, but with needle 76 being offset from the central longitudinal axis of each tubular shaft 74. Needle 76 of inner member 22 shown in FIG. 23 is movable along groove 68, such as that shown in fixed lower jaw 20 of FIG. 21, but is hollow and has a beveled distal opening 80 for allowing passage of fluids as described above. Needle-like protrusion 76 of inner member 22 shown in FIG. 24 is solid and is also movable along groove 68 in fixed lower jaw 20 shown in FIG. 21 for protruding distally from aperture 158 when jaws 18 and 20 are closed.

FIG. 25 illustrates the distal end of a modified outer member 14. Slots 15 are formed in the distal end to receive cams 70 and 72 thus maintaining alignment of jaws 18 and 20.

From the above, it will be appreciated that the endoscopic instrument of the present invention permits multiple functions to be performed endoscopically by use of a forceps unit having a tubular member with jaws configured for grasping or holding objects such as anatomical tissue or needles and an inner member telescopically fitted within the forceps unit tubular member and carrying a needle. The tubular member and jaws of the forceps unit are preferably formed as an integral one-piece construction and are movably disposed within an outer tubular member to permit sliding movement of the outer tubular member over the jaws. The outer member and tubular forceps member can be mounted on a housing and coupled using any suitable handle mechanism and linkages for producing relative movement between the jaws and the outer tubular member. The inner member can also have hollow tubular shafts open at a distal end for facilitating visualization with a conventional endoscope, illumination with fiber optics or other suitable light sources, for passage of implements such as blades or ligature appliers and/or for introducing or collecting fluids prior to, during or after an operative step, such as cutting or puncturing, is completed. When a tubular shaft is closed at a distal end and a hollow needle extends from an opening in the closed distal end, the inner member can be used for precisely administering medicaments such as vasoconstrictors (e.g., epinephrine) or other fluids to an operative site, or for passing lengths of suture material through the hollow needle to suture tissue within the anatomical cavity.

Jaws 18 and 20 of the present invention can be straight, curved and/or angled and can have integrally formed or removable inserts with configurations for grasping and holding tissue and objects such as needles. Note that, while the jaws are discussed generally above as part of forceps for grasping tissue, the jaws can be used to grasp a needle or other object for suturing or the like. Therefore, the term "forceps" as used herein refers to a device for grasping various objects or tissue. The inserts can have any combination or number of longitudinal grooves formed in the inserts for accommodating medical implements. The grooves can extend part way to define stops or abutments limiting distal movement of the needle or can extend the complete length of the inserts to form openings or apertures at a distal end of the jaws to allow passage of the needle beyond the distal end of the jaws when the jaws are closed. The grooves can also have deepened portions to define a stop for a base supporting the needle.

The jaws can have any shape in cross-section when closed, including circular, elliptical, rectangular and polygonal configurations, and can have opposed arcuate or concave portions for clamping tubular objects without compressing the objects. Integral blades can be carried by one or both jaws and can be centrally located for cutting anatomical tissue or can be offset laterally from the central longitudinal axis of the jaws to permit better visualization and the formation of a longitudinal groove for passage of other operating members through the jaws. If a single blade is carried by one jaw, the other jaw can carry an opposed blade in a manner to permit sliding contact with scissor-like cutting, direct abutment of cutting edges to produce a chopping cut, and/or can form a pocket for receiving the cutting edge of the opposed blade to permit partial or complete closure of the jaws together.

When the jaw inserts are removable, the empty cavities defined by the jaws can be used for accommodating cartridges holding surgical staples or clips such that by closing the jaws the staples or clips can be applied to anatomical tissue. Moreover, the elongate tubular structure of the inner member permits a series of cartridges to be carried therein for being applied individually within the anatomical cavity without removal of the inner member.

The position of the electrical connector opposite the handle is merely exemplary of the many various locations at which an electrical connector can be positioned. For example, an electrical connection could be made directly with the housing of the forceps to utilize the forceps jaws as conductive elements for performing electrosurgery. Also, inner surfaces of any of the tubular members, can be electrically insulated to permit passage of electrosurgical instruments therethrough.

The handles and linkages shown and described herein for sliding the outer member over the jaws are exemplary of the types of handle mechanisms suitable for performing the function of closing the jaws. However, the handles can have any configuration for producing relative movement between the outer and intermediate members, including two pivoted legs with finger loops and sliding brackets as disclosed in the parent application, a pistol grip with a movable trigger, or resilient U-shaped members connected between outer and intermediate members. Moreover, the handles can have any orientation relative to the longitudinal axis of the instrument including, for example, substantially transverse orientations whereby the handles extend transversely from a sidewall of the housing or substantially longitudinal orientations whereby the handles extend longitudinally from a rear wall of the housing and are operated like a scissors or even rotatable configurations whereby the handles can be moved between transverse and longitudinal orientations as desired. Suitable linkages include brackets with sliding motion, gears and/or racks mounted on or between handles and the outer and intermediate members, pulleys and cords or any other direct or indirect coupling mechanisms.

The intermediate and outer members can be frictionally fitted to maintain a position by resisting relative movement, can be biased apart with a bias member such as a torsion spring connected between the handles or a helical coil spring disposed around the intermediate member and held in compression between intermediate and outer member flanges, or can be biased together as desired. If the outer tubular member is biased relative to the intermediate member, a mechanism can be provided for opposing or releasing the bias member to permit the outer tubular member to be maintained at any position relative to the jaws, for example by frictional engagement.

The components of the endoscopic instrument of the present invention can be made of any suitable, medical grade materials to permit sterilization for re-use or for single patient use. The components can be made of multiple parts of various configurations and materials to reduce cost. The instrument can have various valves, stop cocks and seals to control fluid flow therethrough, such as valve 158 schematically shown in phantom in FIG. 2.

The features of the various embodiments described above can be combined in any manner desired dependent upon the operational requirements of the procedure to be performed and the complexity of the endoscopic instrument.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A surgical instrument comprising
   a tubular outer member having a proximal end and a distal end;
   an intermediate member having a tubular body disposed telescopically within said outer member, a proximal end and a distal end defining a pair of opposed jaws;
   an inner member slidably disposed at least partly within said intermediate member and comprising a shaft and a needle on a distal end of said shaft; and
   a handle coupled with at least one of said intermediate and outer members and configured to move said jaws between open and closed positions when said distal end of said outer member is moved relative to said jaws.

2. An instrument as recited in claim 1 wherein said jaws define opposed grasping surfaces.

3. An instrument as recited in claim 2 wherein a longitudinal groove is formed in one of said grasping surfaces.

4. An instrument as recited in claim 3 wherein said longitudinal groove extends part way along said one of said grasping surfaces to define a stop limiting distal movement of said shaft and said needle.

5. An instrument as recited in claim 3 wherein said longitudinal groove comprises a shallow portion and a deep portion and a transition between said shallow portion and said deep portion defines a stop limiting distal movement of said shaft and said needle.

6. An instrument as recited in claim 3 wherein said longitudinal groove extends along an entire length of said grasping surface to define an aperture at a distal end of one of said jaws.

7. An instrument as recited in claim 6 wherein said longitudinal groove comprises a shallow portion and a deep portion and a transition between said shallow portion and said deep portion defines a stop limiting distal movement of said shaft and said needle.

8. An instrument as recited in claim 2 wherein a longitudinal groove is formed in each of said opposed grasping surfaces.

9. An instrument as recited in claim 8 wherein said longitudinal grooves extend part way along said grasping surfaces to define a pair of stops limiting distal movement of said shaft and said needle.

10. An instrument as recited in claim 9 wherein each of said longitudinal grooves comprise a shallow portion and a deep portion and a transition between said shallow portion and said deep portion defines a stop limiting distal movement of said shaft and said needle.

11. An instrument as recited in claim 8 wherein said longitudinal grooves extend along entire lengths of said grasping surfaces to define an aperture at a distal end of said jaws.

12. An instrument as recited in claim 1 and further comprising cam members disposed on outer surfaces of said jaws.

13. An instrument as recited in claim 1 wherein said jaws include opposed arcuate portions defining an opening between said jaws.

14. An instrument as recited in claim 1 wherein one of said jaws is fixed parallel to a longitudinal axis of said intermediate member and the other of said jaws is movable.

15. An instrument as recited in claim 1 wherein said needle is coaxial with said shaft.

16. An instrument as recited in claim 1 wherein said needle is offset from a central longitudinal axis of said shaft.

17. An instrument as recited in claim 1 wherein said shaft is hollow, a distal end of said shaft is open and said needle is solid.

18. An instrument as recited in claim 1 wherein said shaft is hollow, a distal end of said shaft is sealed and said needle is hollow and extends from an opening in said closed distal end of said shaft.

19. An instrument as recited in claim 1 wherein a groove is formed in at least one of said jaws, said needle is mounted on a plate and said plate configured to slide along said groove when said jaws are closed.

20. An instrument as recited in claim 1 further comprising;

safety means for locking said inner member to prevent movement of said inner member relative to said outer member.

21. An instrument as recited in claim 1 wherein said inner member further comprises valve means at a proximal end for controlling passage through said inner member.

22. An instrument as recited in claim 1, wherein said jaws are formed as one piece integrally with said distal end.

23. A method of performing surgical procedures comprising the steps of introducing a tubular member having jaws formed thereon through an opening in an anatomical cavity wall;

grasping anatomical tissue with said jaws;

advancing an inner member having a needle thereon distally through said tubular member; and performing a medical procedure with said needle.

24. A method as recited in claim 23 wherein said performing step includes the step of using said needle to perform at least one of the functions of cauterizing, penetrating, injecting, manipulating, creating suction, dissecting, irrigating and aspirating.

25. A method as recited in claim 23 wherein said introducing step includes closing said jaws by sliding a tubular outer member over at least a portion of said jaws.

26. A method as recited in claim 25 wherein said grasping step includes sliding the outer member proximally with respect to the jaws to permit said jaws to resiliently separate, positioning the anatomical tissue between the jaws and sliding the outer member distally with respect to the jaws to close said jaws around the anatomical tissue.

27. A method of performing surgical procedures comprising the steps of introducing a tubular member having jaws formed thereon through an opening in an anatomical cavity wall;

advancing an inner member comprising a shaft with a needle thereon distally through the tubular member until said needle protrudes distally from the jaws; and performing a medical procedure with said needle.

28. A method as recited in claim 27 wherein said performing step includes using said needle to perform at least one of the functions of cauterizing, penetrating, injecting, dissecting, manipulating, creating suction, irrigating and aspirating.

29. A method as recited in claim 27 wherein said introducing step includes closing said jaws by sliding a tubular outer member distally with respect to the jaws and said advancing step includes the step of moving the needle along a groove formed in the jaws.

30. A surgical instrument comprising a tubular outer member having a proximal end and a distal end, a channel being defined through said outer member;

an intermediate member having a body disposed at least partly within said outer member, a proximal end and a distal end having a pair of opposed jaws;

an inner member slidably disposed at least partly within said channel and comprising a shaft and a needle on a distal end of said shaft; and a handle coupled with at least one of said intermediate and outer members and configured to move said jaws between open and closed positions.

31. An instrument as recited in claim 30, wherein said intermediate member extends through said channel and a passage is defined through said intermediate member.

* * * * *